United States Patent [19]

Flanagan

[11] Patent Number: 5,718,583
[45] Date of Patent: Feb. 17, 1998

[54] GINGIVAL CORD-PACKING INSTRUMENT

[76] Inventor: Dennis F. Flanagan, 1671 W. Main St., Willimantic, Conn. 06226

[21] Appl. No.: 576,217

[22] Filed: Dec. 22, 1995

[51] Int. Cl.$^6$ .................................................. A61C 3/00
[52] U.S. Cl. ............................................................. 433/141
[58] Field of Search ................................ 433/136, 141, 433/146, 163, 164

[56] References Cited

U.S. PATENT DOCUMENTS

| | | | |
|---|---|---|---|
| 4,396,375 | 8/1983 | Gores | 433/141 |
| 5,022,859 | 6/1991 | Olivia | 433/141 |
| 5,358,403 | 10/1994 | Groth | 433/136 |

FOREIGN PATENT DOCUMENTS

| | | | |
|---|---|---|---|
| 3539892 | 5/1987 | Germany | 433/141 |

*Primary Examiner*—Ralph Lewis
*Attorney, Agent, or Firm*—Ira S. Dorman

[57] ABSTRACT

A Gingival cord-packing instrument has an elongate handle, and opposite end sections for engaging the gingival cord. At least one of the end sections of the instrument constitutes a blade that is so dimensioned and configured as to enable gentle displacement of the gingiva from the adjacent tooth, for effective insertion of the cord. The end sections of the instrument will generally extend in opposite direction and in mutually parallel planes, lying obliquely to the handle axis, with the blades being so oriented as to cause grooves formed in their tip elements to extend in mutually perpendicular planes.

4 Claims, 2 Drawing Sheets

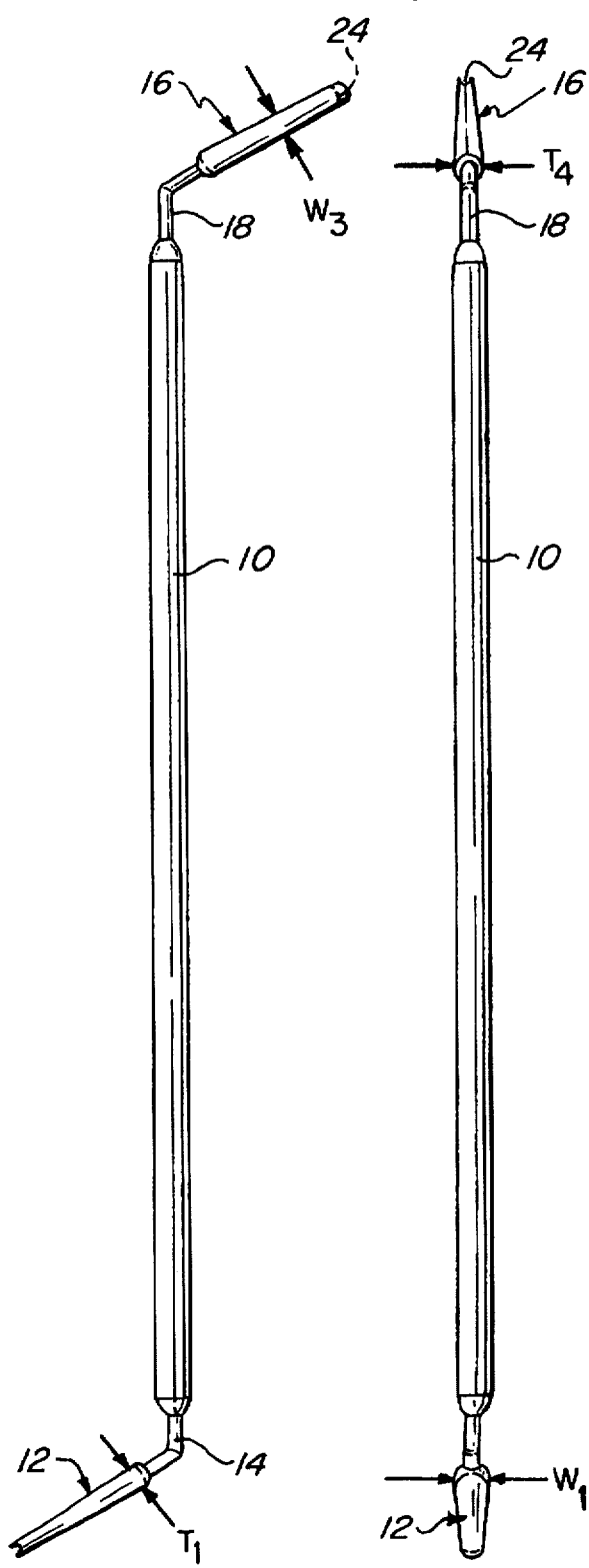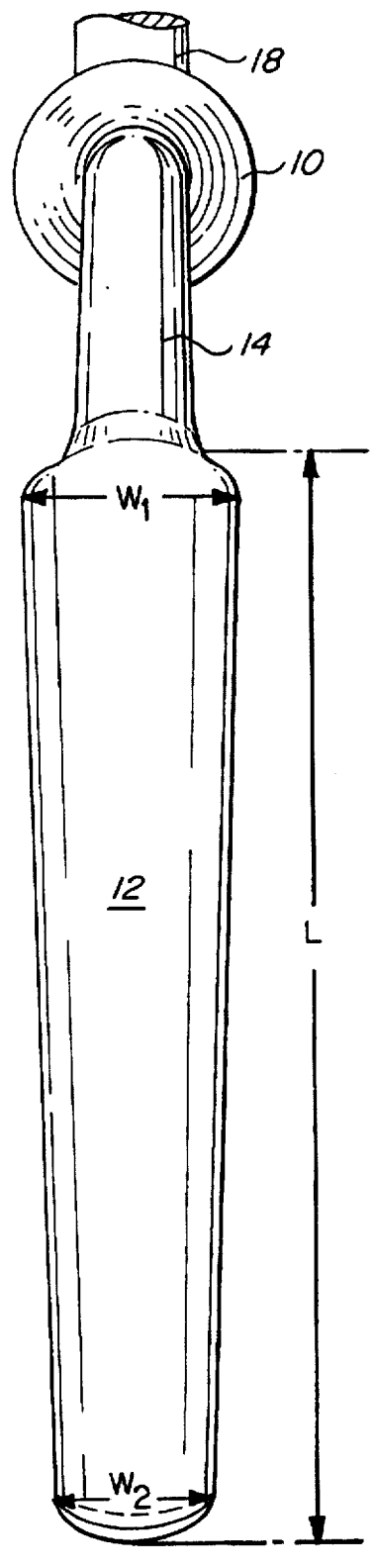

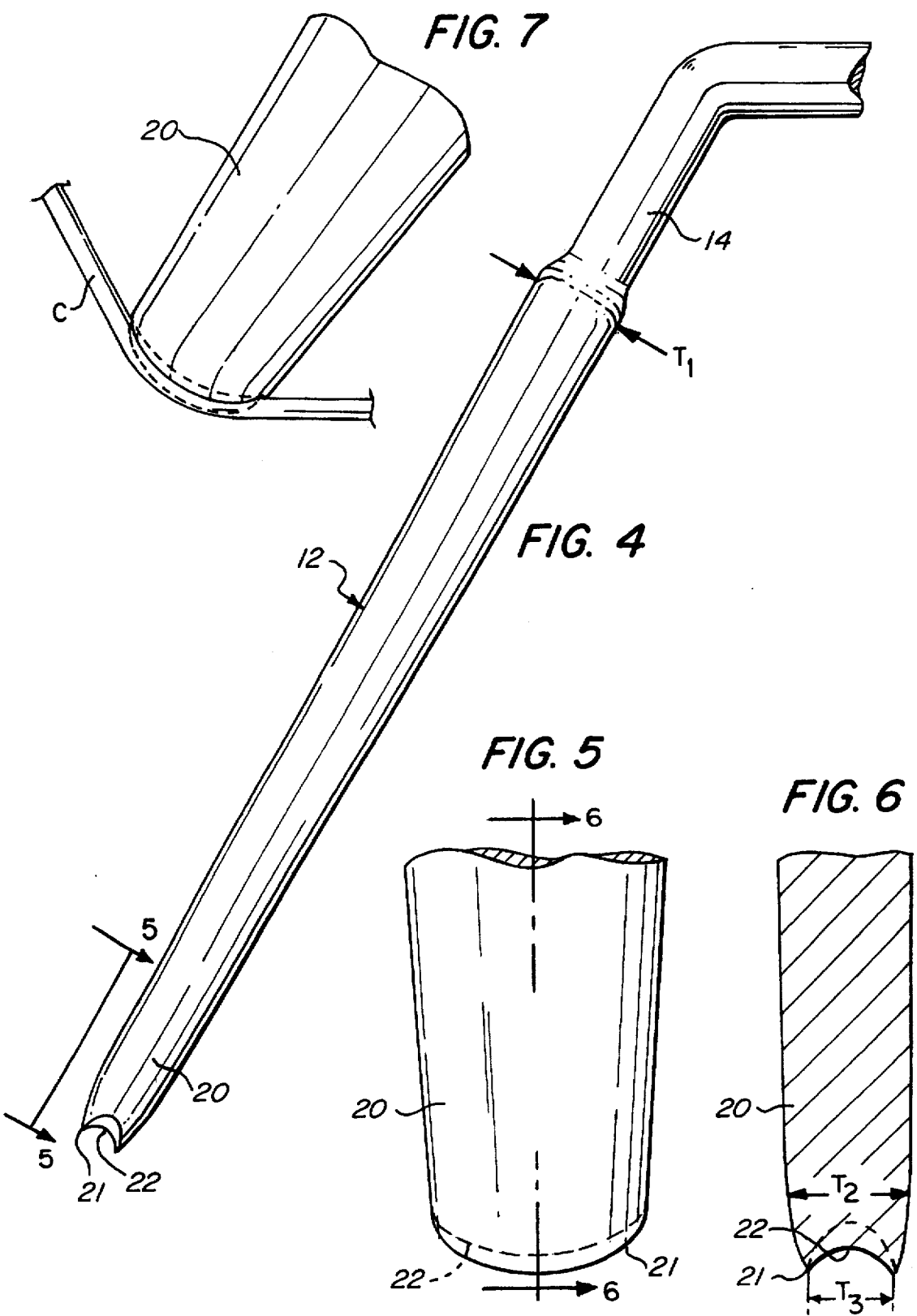

5,718,583

1

GINGIVAL CORD-PACKING INSTRUMENT

BACKGROUND OF THE INVENTION

Gingival cord is used by dentists for introducing drugs into the pocket between a tooth and the adjacent gingiva. Displacement of the gingiva is necessary to allow filling of the pocket deeply and with a maximum amount of cord, and it is desirably done as gently and with as little discomfort to the patient as possible. Instruments presently available do not effectively achieve those ends.

SUMMARY OF THE INVENTION

Accordingly, it is the broad object of the present invention to provide a hand-held dental instrument which is especially adapted for the effective placement and insertion of gingival cord. More specific objects of the invention are to provide such an instrument by which the gingiva can be displaced from the tooth in a gentle manner, which instrument is of incomplex design and inexpensive manufacture.

It has now been found that the foregoing and related objects of the invention are attained by the provision of a hand-held dental instrument that is comprised of an elongate handle section having first and second opposite end sections connected thereto. Each of the end sections includes a cord-engaging portion that extends outwardly of the handle section, at an obtuse angle to its longitudinal axis, and that terminates in a tip element having length, width and thickness dimensions. The tip element has a terminal edge on its free outer end, along which a groove extends in the width direction. The terminal edge and the groove of the first end section tip element are both of convex, arcuate form, and the tip element itself is substantially wider than it is thick; it is oriented generally on a first plane that extends transversely of the handle section axis (at the obtuse angle referred to), and is tapered toward the first plane, in the outward direction. The tip element of the second end section is substantially narrower and thinner than the first end section tip element is wide, and it is oriented generally on a second plane, in which the longitudinal axis of the handle section also lies. The length and width dimensions of the first and second section tip elements lie parallel to the first and second planes, respectively, and the thickness dimensions thereof lie normal to the respective planes.

In preferred embodiments, the tip element of the first end section will additionally be tapered, in the outward direction, toward a third plane which is oriented perpendicular to the first plane, and the tip element will be integrally formed as an element of a substantially flat blade, the latter constituting the cord-engaging portion of that section of the instrument. The cord-engaging portion of the second end section will usually also comprise a blade having the tip element integrally formed thereon, which blade will advantageously taper, in its outward direction, toward both the second plane and also toward a fourth plane to which the second plane is perpendicular. The fourth plane will usually be disposed parallel to the first plane defined, such that the end sections of the instrument will be offset from the handle section in opposite directions. Each end section will generally be formed to include a shank element by which the blade thereof is joined to the handle section, and the instrument itself will normally be integrally formed as a single piece.

BRIEF DESCRIPTION OF THE DRAWINGS

FIG. 1 is a side view of a dental instrument embodying the present invention;

2

FIG. 2 is a view of the instrument of FIG. 1, rotated 90° about the axis of its handle;

FIG. 3 is a fragmentary end elevational view of the instrument of the foregoing Figures, drawn to a greatly enlarged scale;

FIG. 4 is a fragmentary side elevational view showing the cord-engaging blade portion at the same end of the instrument, drawn to the same scale;

FIG. 5 is a fragmentary end elevational view of the tip element on the blade portion shown in FIGS. 3 and 4, taken along line 5—5 of FIG. 4 and drawn to a further enlarged scale;

FIG. 6 is a sectional view of the tip element taken along line 6—6 of FIG. 5; and FIG. 7 is an end elevational view of the same tip element, shown in engagement with a fragmentarily illustrated cord.

DETAILED DESCRIPTION OF THE PREFERRED AND ILLUSTRATED EMBODIMENT

Turning now to detail to the appended drawings, therein illustrated is a gingival cord-packing instrument embodying the present invention and consisting of a handle section 10, a first blade portion, generally designated by the numeral 12, connected at one end of the handle section by an offsetting shank portion 14, and a second blade portion, generally designated by the numeral 16, connected at the opposite end of the handle section 10 by a second offsetting shank portion 18. The blade portions 12 and 16 extend oppositely and in generally parallel planes, each of which planes is oriented at an obtuse angle, typically of about 120°, to the longitudinal axis of the handle section 10.

As is best seen in FIG. 3, the blade portion 12 tapers from a first width dimension $W_1$ to a second width dimension $W_2$, the values of which dimensions will typically be about 2.0 mm to 2.25 mm, and 1.5 mm, respectively. The blade portion 12 also tapers in its thickness dimension, diminishing from a dimension $T_1$ to a dimension $T_2$ near its free end, and then more sharply to a terminal edge dimension $T_3$; typically the respective thickness values will be 1.0 mm, 0.5 mm and 0.3 mm. The length L of the blade portion 12 will typically be about 12 mm, and the overall length of the shank portion 14 will typically be about 3 mm.

The terminal edge 21 of the tip element 20 is of convex arcuate form, as is the groove 22 formed therein and extending from side-to-side (i.e., in the width direction) therealong; groove 22 is also arcuate in cross section. The shape and configuration of the groove 22 affords secure engagement of the cord C, and the tapered profile of the tip element 20, as established by the thickness dimensions $T_1$, $T_2$ and $T_3$, enables its effective insertion. Thus, force upon the instrument will gently displace the gingiva from the adjacent tooth, allowing deep insertion of the cord and a maximal packing volume; this in turn maximizes the amount and the thoroughness of distribution of the drug carried to the treatment site.

Although not illustrated in the same detail, it can be seen that the cord-engaging blade portion 16 at the opposite end of the instrument is tapered in both its width dimension (designated for convenience by the single value $W_3$) and also its thickness dimension (designated by the single value $T_4$). The tip element on the portion 16 is generally narrower and thinner than the tip element 20, on the blade portion 12, is wide. A groove 24 extends from side-to-side (i.e., in the width dimension) across the terminal edge of the blade portion 16, and it too is of arcuate configuration and cross section. It should be appreciated that the groove 24 extends in a plane that is perpendicular to that in which the groove 22 extends, thereby affording to the dentist a high degree of control and latitude in manipulating the cord, to achieve optimal insertion both along the lateral gum lines and also between adjacent teeth.

The instrument will usually be integrally formed as a single piece, using a suitable grade of steel of the like; other materials and constructions may of course also be employed, if so desired. It will also be appreciated that an instrument may deviate from the specific embodiment described herein without departure from the inventive concepts of the instant specification.

Thus, it can be seen that the present invention provides a hand-held instrument which is especially well adapted for the effective placement and insertion of gingival cord. The instrument enables gentle displacement of the gingiva from an adjacent tooth, and it is of incomplex design and inexpensive manufacture.

Having thus described the invention, what is claimed is:

1. A hand-held dental instrument for use in inserting gingival cord, comprising:

a substantially straight elongated handle having opposite first and second ends, a blade member having first and second ends, and a shank element disposed between said first end of said handle and said first end of said blade member, said shank element being constructed to cause said blade member to extend away from said handle at an obtuse angle to the longitudinal axis of said handle, said blade member having two opposing substantially flat surfaces, each bounded by said blade member's first and second ends and by two spaced-apart side edges, said opposing substantially flat surfaces having a common length extending between said blade member's first and second ends and a common width extending between said spaced-apart side edges, wherein said width decreases from said blade member first end to said blade member second end, said opposing substantially flat blade surfaces being separated from one another by a thickness which decreases from said blade member's first end to said blade member's second end, said blade member thickness decreasing sharply at said blade member second end and forming a terminal edge which curves convexly between said spaced-apart side edges, said terminal edge having a groove extending between said spaced-apart side edges for engaging the gingival cord for insertion in a patient's mouth.

2. The instrument of claim 1, integrally formed as a single piece.

3. A hand-held dental instrument for use in inserting gingival cord, comprising:

a substantially straight elongated handle having opposite first and second ends, a blade member having first and second ends, and a shank element disposed between said first end of said handle and said first end of said blade member, said shank element being constructed to cause said blade member to extend away from said handle at an obtuse angle to the longitudinal axis of said handle, said blade member having two opposing surfaces, each bounded by said blade member's first and second ends and by two spaced-apart side edges, said opposing surfaces having a common length extending between said blade member's first and second ends and a common width extending between said spaced-apart side edges, wherein said width decreases substantially from said blade member first end to said blade member second end, said opposing blade surfaces being separated from one another by a thickness which is substantially greater at said blade member's first end than at said blade member's second end, said blade member second end forming a terminal edge which curves convexly between said spaced-apart side edges, said terminal edge having a groove extending between said spaced apart side edges for engaging the gingival cord for insertion in a patient's mouth.

4. The instrument of claim 3 wherein said blade member thickness decreases sharply at said blade member second end to form said terminal edge.

* * * * *